(12) United States Patent
Coleman et al.

(10) Patent No.: US 7,118,525 B2
(45) Date of Patent: Oct. 10, 2006

(54) IMPLANTABLE CARDIAC ASSIST DEVICE

(76) Inventors: Edward J. Coleman, 905 S. Monroe Ave., Green Bay, WI (US) 54301; Gerard T. Coleman, 5501 Swan Dr., Galveston, TX (US) 77551; William T. Neill, 730 Brinsmere Dr., Elm Grove, WI (US) 53122

( * ) Notice: Subject to any disclaimer, the term of this patent is extended or adjusted under 35 U.S.C. 154(b) by 0 days.

(21) Appl. No.: 10/829,573

(22) Filed: Apr. 22, 2004

(65) Prior Publication Data

US 2004/0225177 A1 Nov. 11, 2004

Related U.S. Application Data

(60) Provisional application No. 60/464,766, filed on Apr. 23, 2003.

(51) Int. Cl.
*A61N 1/36* (2006.01)
(52) U.S. Cl. ....................................................... 600/16
(58) Field of Classification Search .................. 600/16, 600/17; 601/11, 15, 151–153
See application file for complete search history.

(56) References Cited

U.S. PATENT DOCUMENTS

| | | | |
|---|---|---|---|
| 4,902,291 A | 2/1990 | Kolff | |
| 4,957,477 A | 9/1990 | Lundbäck | |
| 5,119,804 A | 6/1992 | Anstadt | |
| 5,131,905 A | 7/1992 | Grooters | |
| 5,169,381 A | 12/1992 | Snyders | |
| 5,250,167 A | 10/1993 | Adolf et al. | |
| 5,256,132 A | 10/1993 | Snyders | |
| 5,271,746 A | 12/1993 | Pol et al. | |
| 5,273,518 A | 12/1993 | Lee et al. | |
| 5,389,222 A | 2/1995 | Shahinpoor | |
| 5,397,349 A | 3/1995 | Kolff et al. | |
| 5,429,584 A | 7/1995 | Chiu | |
| 5,533,958 A | 7/1996 | Wilk | |
| 5,713,954 A | 2/1998 | Rosenberg et al. | |
| 5,738,627 A | 4/1998 | Kovacs et al. | |
| 5,749,839 A | 5/1998 | Kovacs | |
| 5,800,334 A | 9/1998 | Wilk | |
| 5,902,229 A | 5/1999 | Tsitlik et al. | |
| 5,908,378 A | 6/1999 | Kovacs et al. | |
| 5,971,910 A | 10/1999 | Tsitlik et al. | |
| 5,971,911 A | 10/1999 | Wilk | |
| 6,109,852 A | 8/2000 | Shahinpoor et al. | |
| 6,238,334 B1 | 5/2001 | Easterbrook, III et al. | |

(Continued)

OTHER PUBLICATIONS

Abiomed, 25 web pages, beginning with article, "Ky. Patient gets artificial heart," from www.abiomed.com on Jul. 3, 2001.

(Continued)

*Primary Examiner*—Jeffrey R. Jastrzab
(74) *Attorney, Agent, or Firm*—Jeffrey D. Peterson; Michael Best & Friedrich LLP

(57) ABSTRACT

The present invention relates to therapeutic devices to work in conjunction with a diseased or failing heart to satisfy the hemodynamic needs of a patient. More particularly, the invention relates to a fully implantable device for assisting a heart to pump blood by intermittently applying pressure to at least a portion of the ventricular surface of the heart (if not the entire surface), preferably both the atrial and ventricular surfaces, at predetermined or possibly pre-programmed intervals to assist the heart to provide adequate hemodynamic output by sensing demand of the human body. In short, the present invention assists the maintenance of, or reestablishes, the normal contraction sequence of a healthy heart.

9 Claims, 6 Drawing Sheets

U.S. PATENT DOCUMENTS

| | | | |
|---|---|---|---|
| 6,254,525 B1 | 7/2001 | Reinhardt et al. | |
| 6,258,021 B1 | 7/2001 | Wilk | |
| 6,282,445 B1 | 8/2001 | Reinhardt et al. | |
| 6,464,655 B1 | 10/2002 | Shahinpoor | |
| 6,475,639 B1 | 11/2002 | Shahinpoor et al. | |
| 6,602,182 B1* | 8/2003 | Milbocker | 600/16 |

OTHER PUBLICATIONS

Abiomed, Annual Report, 27 pages from www.abiomed.com on Mar. 15, 2001.

Advanced Technology Development Center-ATDC, 2 web pages about ATDC, from www.atdc.org on Sep. 18, 2002.

Allan, R., "Medtronic sets the pace with implantable electronics," Success Story/Heart Pacemakers, www.elecdesign.com, pp. 52-56 (Oct. 27, 2003). (7-pg. Copy provided is from Web and does not reflect article page numbers).

Anstadt, G. L., et al., "Prolonged circulatory support by direct mechanical ventricular assistance," *Trans. Amer. Soc. Artif. Int. Organs*, vol. XII, pp. 72-79 (1966).

Auricchio, Angelo, et al., "Cardiac resynchronization therapy: current state of the art," *Circulation*, 109:300-307 (2004).

Bar-Cohen, Y., et al., "Electro-active polymer (EAP) actuators for planetary applications," SPIE No. 3669-05, pp. 1-6 (1999).

Bencini, Adriano, et al., "The "pneumomassage" of the heart," *Surgery*, 39:3, pp. 375-384 (Mar. 1956).

Bonsor, Kevin, "How artificial hearts work," 3 pages from www.howstuffworks.com on Jun. 13, 2002.

Bourdon medical device, 1 pg., faxed by client Apr. 20, 2004, source not identified.

Buckberg, Gerald D., "Basic science review: the helix and the heart," *J Thorac Cardiovasc Surg*, 124:5, pp. 863-883 (Nov. 2002).

Burns, W. H., et al., "Hemodynamic studies with a new pulsatile pump," *Trans. Amer. Soc. Artif. Int. Organs*, vol. XI, pp. 65-67 (1965).

Buxton, Denis B., "Recommendations of the National Heart, Lung, and Blood Institute Nanotechnology Working Group," *Circulation*, 108:2737-2742 (Dec. 2, 2003).

Carrington, Russell A. J., et al., "Direct compression of the failing heart reestablishes maximal mechanical efficiency," *Ann. Thorac. Surg.*, 75:190-196 (2003).

The Jarvik 2000 implantable axial-flow left ventricular assist system, *Circulation*, 105:2808-2809 (2002).

Delgado, Diego H., "Mechanical circulatory assistance," *Circulation*, 106:2046-2050 (2002).

Dowling, Robert D., et al., "Operative techniques for implantation of the AbioCor total artificial heart," *OpTechniq Thorac Cardiovasc Surg*, 7:3,139-151 (Aug. 2002).

Endocardial Solutions, "Guiding the direction of cardiac therapies," Annual Report 2002, St. Paul, MN, at www.endocardial.com (7 pages).

Endocardial Solutions, "Endocardial Solutions announces first successful human NAVEX procedure," www.endocardial.com, (Aug. 14, 2002 Press Release), 1 page.

Fauber, John, Pacemaker/defibrillator pair touted, Milwaukee J. Sentinel, 2 pages (May 24, 2004), from www.jsonlin.com.

Fauber, John, "Devices simplify heart repair," Milwaukee J. Sentinel, 2 pages, Nov. 12, 2001, from www.jsonline.com.

Fauber, John, "Heart pump found to dramatically improve patient survival rate," Milwaukee JI. Sentinel, 2 pages, Nov. 13, 2001, from www.jsonline.com.

Fauber, John, "A helping hand for ailing hearts," Milwaukee JI. Sentinal, 4 pages, Aug. 26, 2004, from www.jsonline.com.

First World Congress on Biomimetics and Artificial Muscles, 3 web pages advertising Dec. 9-11, 2002 congress, from www.worldcongress.net on Dec. 8, 2002.

Forman, David, "Companies use trials to prove marketability," *Smalltimes*, p. 40, Sep./Oct. 2002.

Frazier, O. H., et al., "Initial clinical experience with the Jarvik 2000 implantable axial-flow left ventricular assist system," *Circulation*, 105:2855-2860 (2002).

Hall, Stephen S., "Brain Pacemakers," *Technology Review*, pp. 34-43 (Sep. 2001).

Hendry, Paul J., et al., "Implantation technique for the Heartsaver Left Ventricular Assist Device," *Op Techniq Thorac Cardiovasc Surg*, 7:3,152-157 (Aug. 2002).

Hill, J. Donald, "Implantation of the Thoratec Ventricular Assist Device," *Op Techniq Thorac Cardiovasc Surg*, 7:3,158-170 (Aug. 2002).

Huang, Gregory T., "Electroactive polymers," *Technology Review*, p. 32 (Dec. 2002/Jan. 2003).

Johnson, R. Colin, "Robot researchers get some hints from nature," *Electronic Engineering Times*, p. 57 (Sep. 9, 2002).

Karoub, Jeff, "'Stentennas' could signal change in monitoring arteries," *Smalltimes*, pp. 57 (Mar./Apr. 2004).

Karoub, Jeff, "Biotech meets small tech," 2 pages., no publication info available, no date.

Keshavarzi, A, et al., "Blood pressure, pulse rate, and rhythm measurement using ionic polymer-metal composites sensors," SPIE, 3669:369-376 (Mar. 1999).

Kolobow, Theodor, and Bowman, Robert L., "Biventricular cardiac assistance energized by suction actuated recoil of a single constricting rubber ventricle," *Trans. Amer. Soc. Artif. Int. Organs*, vol. XI, pp. 57-67 (1965).

Magovern, James A., et al., "Implantation of the TandemHeart Percutaneous Left Ventricular Assist Device," *Op Techniq Thorac Cardiovasc Surg*, 7:3, 112-119 (Aug. 2002).

Medfacts, "Understanding heart valve surgery," 3 pages, from www.crdiodoc.com on Mar. 15, 2001.

Medtronic, "Medtronic announces FDA approval of new GEM® III AT Defibrillator with atrial therapies," Press Release, www.medtronic.com (Feb. 13, 2001), 3 pages.

Medtronic, Press Release, "Medtronic announces first implant of over-the-wire-left-heart lead to treat heart failure," 3 pages from www.medtronic.com, on Mar. 20, 2001.

Menicanti, Lorenzo, et al., "The Dor procedure: what has changed after fifteen years of clinical practice?," *J Thorac Cardiovasc Surg*, vol. 124: 886-890 (2002).

Methodist Hospital, et al. "The Methodist Hospital and Baylor College of Medicine surgeons implant first U.S. patient with MicroMed DeBakey Ventricular Assist Device™", Methodist Health Care System, Houston, TX, http://www.methodisthealth.com/vad., 3 pages (Jun. 8, 2000).

Micromed Technology, Inc., www.micromed.com, "The MicroMed DeBakey VAD," 3 pages, printed from Internet Mar. 16, 2001.

Noon, George P., et al., "Implantation of the MicroMed DeBakey VAD," Michael E. DeBakey Dept Surg, DV Transpl & Assist Devices, Baylor, Houston, TX, Elsevier Science (USA), 1522-2942/02/0703-0000, pp. 126-138 (2002).

Orlando, FL., newspaper article, "New pacemaker can aid those with heart failure," no date.

Philadelphia International Medicine News Bureau, 6 web pages regarding ACORN Cardiac Support Device, from www.philadelphiaintmed.com on Oct. 5, 2001.

Saavedra, W. F., et al., "Reverse remodeling and enhanced adrenergic reserve from passive external support in experimental dilated heart failure," *J. of Amer. College of Cardiology*, 39:12, pp. 2069-2076 (Jun. 19, 2002).

St. Judes, "St. Jude heart valve recall," 2 pages, from www.stjude.com on Mar. 15, 2001.

Sidawi, Danielle, "Medical applications adopt MEMS technology," *R&D Magazine*, pp. 48-49 (Feb. 2004).

Stuart, Candace, "Obstacles clutter path for implant sector," *Smalltimes*, p. 36, Sep./Oct. 2002.

Technology Review, "Setting the pace," author unknown, p. 96 (Sep. 2001).

Texas A&M University, Biomedical Engineering Program, "This web page is meant to provide access to links about several different types of heart assist medical devices or procedures," 7 pages from www.biomed.tamu.edu on Mar. 16, 2001.

Texas Heart Institute, "Official statement of the Texas Heart Institute and St. Luke's Episcopal Hospital," Apr. 11, 2000. (2 pages from www.tmc.edu on Jun. 13, 2002).

Texas Heart Institute, "FDA approves heart-assist device first tested at Texas Heart Institute," 2 pages, Oct. 7, 1998, from www.tmc.edu on Jun. 13, 2002.

Thoratec, "Circulatory support products commercially available in the United States," 1 page, from website www.thoratec.com on Nov. 13, 2001.

University of Iowa Health Care, "Optimizing treatment of patients with advanced heart failure," 5 pages from www.uihealthcare.com on Mar. 15, 2001.

Van Nostrand's Scientific Encyclopedia, 8th ed. (1995) (4 pages: 2 front cover pages, and 2 pages which define a Bourdon Tube).

Verrengia, Joseph B., "Cell injections might fix heart damage," AP Science Writer, 2 pages, published Apr. 6, 2001. Copy obtained from www.ararillonet.com.

Vineberg, Arthur, "Short communications: mechanical heart massager," *Canad. M.A.J.*, vol. 77, pp. 495-498 (Sep. 1, 1957).

Voss, David, "Smart home care," Technology Review, publication/date unknown, 1 page.

Wechsler, Andrew S., et al., Editorial, "Video comes to the Journal," *J Thorac Cardiovasc Surg*, 124:5, pp. 884-885 (Nov. 2002).

Wolcott, Mark W., et al., "A mechanical heart massager: a preliminary report," *Surgery*, 48:5, pp. 903-906 (Nov. 1960).

\* cited by examiner

IMPLANTABLE CARDIAC ASSIST DEVICE

CROSS-REFERENCE TO RELATED APPLICATIONS

This application claims priority to U.S. Provisional Patent Application Ser. No. 60/464,766, filed Apr. 23, 2003, that application being incorporated herein by reference, in its entirety.

STATEMENT REGARDING FEDERALLY SPONSORED RESEARCH OR DEVELOPMENT

Not applicable.

FIELD OF THE INVENTION

The present invention relates to therapeutic devices to work in conjunction with a diseased or failing heart to satisfy the hemodynamic needs of a patient. More particularly, the invention relates to a fully implantable device for assisting a heart to pump blood by intermittently applying pressure to at least a portion of the ventricular surface of the heart (if not the entire surface), preferably both the atrial and ventricular surfaces, at predetermined or possibly pre-programmed intervals to assist the heart to provide adequate hemodynamic output by sensing demand of the human body. In short, the present invention assists the maintenance of, or reestablishes, the normal contraction sequence of a healthy heart.

The present device is designed to restore to normal the electrical excitation pathways and mechanical contraction sequence of the failing heart. Where necessary, this restores the normal spread of electrical excitation pathways with a phased array electrical stimulation coupled with a phased array mechanical compression to restore the normal excitation/contraction sequence to a failing heart.

BACKGROUND OF THE INVENTION

The human heart is a very complex organ that relies on both mechanical and electrical operation in order to perform properly. As with any complex mechanism, problems can and often do arise, with the heart. For example, over time the electrical pathways in the heart (which sequentially cause the atria and ventricles to contract) may fail, thereby causing the heart to lose its rhythm, which is known as arrhythmia. In that event, the ventricles will contract at improper times, and as a result the output of blood decreases. In addition, in some failing hearts the muscle of the heart no longer contracts the ventricles to a sufficient extent. Insufficient ventricular contraction can produce a dangerous reduction in the amount of blood flow.

Numerous attempts have been made to assist these diseased or failing hearts by applying external pressure directly to the heart. One such example is direct manual compression of the heart by a person's hand during open chest cardiopulmonary resuscitation. Often, however, the patient requires cardiac or circulatory support or assist for extended periods of time, such as hours, days, weeks, or for the rest of the patient's life. Thus, manual manipulation of the heart is not a solution to the problem in most cases.

Mechanical devices have been developed to apply external pressure directly to the heart. Some of these devices utilize an inflatable liner that surrounds the heart. For example, U.S. Pat. No. 5,119,804 Anstadt discloses a cup that is provided with an elastomeric liner. The heart is held in place within the liner, which is cyclically inflated and deflated to apply external pressure to the heart. While this device provides an improvement in hemodynamics for a diseased or failing heart, the device is not fully implantable. U.S. Pat. No. 5,131,905 Grooters and U.S. Pat. No. 6,238,334 Easterbrook, III et al. are further examples of external (as opposed to implantable) cardiac assist devices.

U.S. Pat. No. 6,464,655 Shahinpoor, at FIG. 6$d$ and FIG. 7, illustrates an embodiment of the "Electrically-Controllable Multi-Fingered Resilient Heart Compression Device" disclosed therein. In the embodiment shown artificial muscles, specifically electro-active polymers, are used to create "soft fingers" that can be directly electrically powered and computer controlled by wires. See eg., U.S. Pat. No. 6,464,655 at column 8, lines 19–38, : The teachings of Shahinpoor are specifically incorporated by reference herein.

Another shortcoming inherent in the prior art devices results from the fact that relatively high pressures are applied almost exclusively to the central portion of the ventricles' outer surfaces. This causes the heart to deform into an unnatural, generally hourglass, shape and may even eventually cause trauma (e.g., bruises) to the heart, especially if one of the prior art devices is operated for an extended period of time.

It is an object of the present invention to provide a device which does not interfere with the normal contraction pattern or rhythm of the heart as long as the "normal" pattern provides sufficient cardiac output of blood (e.g., from about 1.5 to about 3 liters per minute) to sustain and support the activities in which the patient wishes to engage. However when normal cardiac output is insufficient to sustain day-to-day activities the present device provides cardiac assist by increasing blood flow by compressing the heart mechanically or hydraulically from the apex or tip of the heart to its base (or top) without abnormal compression of generally the middle portion of the heart.

It also is one aspect of the present invention to provide a generally cone-shaped, fully-implantable cardiac cuff, or cup, or incompressible or supporting envelope for efficiently assisting the mechanical compression of the heart. It is another aspect to operate such a cardiac cup without unduly deforming the natural shape of the heart during the mechanical or hydraulic compression of the heart.

It is a further object of the present invention to provide a fully implantable cardiac cup for assisting heart function, which applies substantially uniform fluid pressure against the exterior surface of at least a portion of the ventricular portion of the heart during the systolic phase.

It is yet a further object of the present invention to provide a cardiac cup for assisting a heart function that can be installed in its operative position with minimal movement of the heart. Generally speaking the device will be sutured or otherwise attached to the heart so as to prevent device migration during use.

It is another object of this invention to provide a fully-implantable pressure vessel and pacing device.

BRIEF DESCRIPTION OF THE INVENTION

Briefly, in one aspect, the present invention is a fully implantable cardiac massage apparatus. A cardiac massage apparatus of this invention is, in one aspect, an chamber array, the array comprising a series or locus of spaced-apart, fluidically coupled, chambers or helices. In one aspect an array of this invention comprises helically-wound chambers, helices, or loops located closely adjacent or on the epicardium. The array further has fluid input and output ports. The chambers or helices collectively define an interior surface which closely conforms to the exterior surface of a heart when implanted. In one embodiment the array fluid input port is located adjacent to the apex of the heart to be massaged and the fluid output port is located adjacent to the base of the heart to be massaged.

An apparatus of the present invention further includes coupled valve means, pump means, controller means, and cardiac activity sensor/input means. The valve means is fluidly or hydraulically coupled to the chamber array input port and output port and, in turn, is coupled to the pump means. The pump means and valve means are both electronically coupled to the controller means. In one aspect, the controller means is an electronically-powered microprocessor. A controller means of the present invention is adapted to actuate the pump means and valve means so that fluid is pumped substantially continuously through the input port while intermittently cycling the discharge. In this manner the fluidly-coupled chambers or helices are inflated and deflated starting at the apex of the heart and continuing toward the base of the heart to create a rhythmic cardiac massage which substantially imitates the natural contraction sequence of the heart.

A cardiac massage apparatus of the present invention further includes a cardiac activity sensor/input means which monitors or senses cardiac output and inputs that information to the controller means so that the controller means can determine whether additional cardiac output is needed and can initiate the above-described cardiac massage or compression.

In a preferred practice, the helically-wound or helical chamber array comprises a series of spaced-apart chamber segments which are fluidically coupled. In a further preferred practice massage apparatus includes a separately-implanted source of electrical energy such as, for example, a rechargeable battery and an optional fluid reservoir. The chamber segments are disposed over the exterior of the heart in a helical array.

BRIEF DESCRIPTION OF THE DRAWINGS

Some of the features and advantages of the invention having briefly been stated, others will appear from the detailed description which follows, when taken in connection with the accompanying drawings in which.

DETAILED DESCRIPTION

While the present invention will be described more fully hereinafter with reference to the accompanying drawings, in which particular embodiments are shown, it is to be understood at the outset that persons skilled in the art may modify the invention herein described while still achieving the favorable results of this invention. Accordingly, the description which follows is to be understood as a broad teaching disclosure directed to persons of skill in the appropriate arts and not as limiting upon the present invention.

Figure 1:
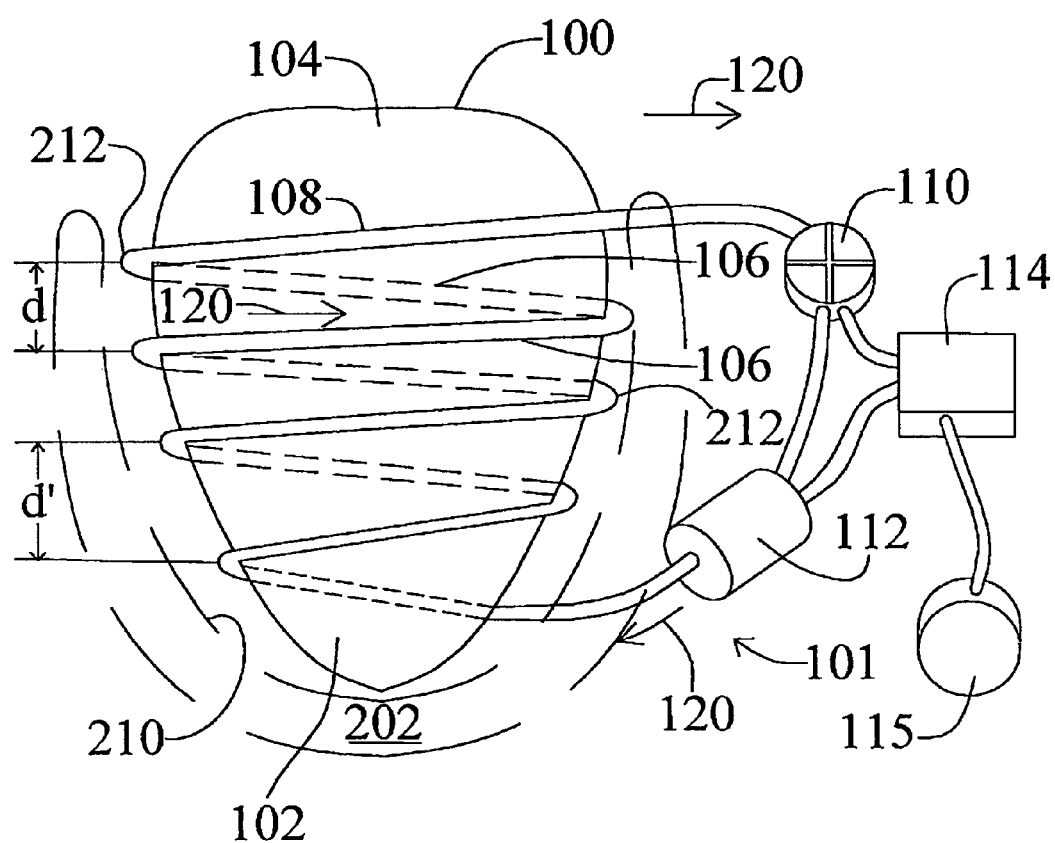
FIG. 1 is a perspective view of an apparatus of the present invention.

Thus there is shown in FIG. 1 an embodiment of an apparatus or cardiac assist device 101 of the present invention. A patient's heart 100 is shown schematically. Enveloping or enshrouding heart 100 from its apex 102 to its base 104 is a helically wound length of tubing or a bladder array 106, the tubing segments on the back side of heart 100 being shown in dashed lines. Alternatively, the array 106 could comprise an arrangement, locus, or series of fluidically coupled chambers. The individual helices 108 of the tubing array 106 shown in FIG. 1 are separated by distances d and d': Distances d, d' are variable and can be adjusted by the physician (e.g., by selecting a device with wider or narrower "d" spacing) to create a more natural mimic of the heart's rhythmic contractions as is described below. Also shown in phantom in FIG. 1 is an optional heart-shaped, supporting cup or envelope 202. The heart-shaped cup member 202 is constituted of a somewhat rigid, but flexible material. The material (preferably translucent) of cup-shaped member 202 should have adequate rigidity so that it does not collapse during diastolic actuation. Further, it should not expand radially to any great extent when pressurized fluid is introduced into chambers 108 in accordance with the method of the present invention. As is shown in FIG. 1, the inside surface 210 of cup 202, in this embodiment, is in contact with the outer-most surface of chambers 108 so as to support them, to keep the segments or chambers separated from each other, and to direct inwardly (to compress heart 100) any pulsatile or pump surge input thereto.

Also shown in FIG. 1 to be in fluid communication with chamber array 106 are a pressure regulator 110 and a pump 112. The regulation of chamber pressure may be achieved by a relief valve coupled to the fluid circuit, a pressure regulator, or possibly, by "pump surge." Pressure regulator 110 and pump 112 are electrically coupled to a controller means or module 114, e.g., a microprocessor. (Under circumstances where added complexity is permissible, a solenoid valve could be substituted for a pressure regulator 110). Microprocessor 114 is programmed to receive input information as to the status and performance characteristics of heart 100 from a cardiac activity sensor/input means 115. Assuming heart 100 is providing adequate cardiac output i.e., it is beating sufficiently frequently, with sufficient efficiency, the assist system shown in the FIG. 1 provides no stimulation or assistance to heart 100. However when microprocessor 114 receives input that the cardiac output of heart 100 is inadequate for the patient's activity, microprocessor 114 activates pump 112 and valve 110.

Pump 112 causes a fluid, preferably an incompressible, low viscosity, biocompatible fluid such as saline to flow into the individual helices 108 starting at the heart's apex 102 and flowing toward its base 104. (It is conceivable that compressed gas could be used to activate the helices or chambers according to this invention). This creates a wave form or wave front which travels from the apex toward the base which causes the heart (specifically the ventricles) to contract in rhythmic fashion. This contraction wave form tends to mimic normal cardiac depolarization but with enhanced or accelerated fluid blood flow from the ventricles. The speed of pump 112 (which preferably is either a kinetic or centrifugal pump, a peristaltic or positive displacement pump but may be of any type including axial turbine or a radial pump) is coordinated with pressure regulator 110 to create a sequence or series of wave forms or pulses of fluid in chambers 108 causing at least the ventricles (but preferably both the ventricles and the atria) to be rhythmically massaged or compressed. In this manner cardiac output is substantially enhanced with the assistance of this device. A device of this invention has the capability of assisting left and right ventricles (i.e., compressing or massaging) essentially simultaneously or sequentially.

The intensity of the compression step can be adjusted by adjusting pump speed and pressure regulator 110 timing. The intensity of the compression step can also be adjusted by the selection of stiffness and diameter of the bladder or tube elements used to create the array 106. The number of chambers 108 wrapped around heart 100 and their separation distance (discussed above), also determines the intensity and extent of assist provided to the heart. One skilled in the art will appreciate that some amount of experimentation regarding bladder characteristics may be needed to optimize the natural pumping efficiency of the heart using a device of this invention.

It also is to be appreciated that the physiological factor (or factors) observed or monitored by sensor/input means 115 to provide input to control means 114 may include many (if not all) of the parameters normally observed appurtenant to electrical sensing and/or pacing of the heart. Thus general body activity, oxygen saturation, pulse, peak-to-peak T-wave separation and numerous other indicia of cardiac activity may be observed in order to trigger e.g., via the microprocessor 114, the use of the present device. Appropriate input leads, whether internal or external to the heart, are selected depending upon the parameter(s) of cardiac activity selected to be observed or monitored. To some extent, the overall placement and configuration of the chamber array may be modified in view of the physiologic factor or factors chosen to be monitored.

It is possible that the sensor/input means 115 to control means 114 could be the electronic output of a device which measures cardiac output i.e., blood flow or blood volume, directly.

Various sensors e.g., cardiac sensing/pacing leads, which measure cardiac output directly or indirectly, are available from Medtronic, Inc., in Fridley, Minn., U.S.A. Cardiac output also can be measured using a sensor inserted into an artery at the wrist.

It also is within the contemplation of this invention that the input 115 to control means 114 could be the output from a cardiac pacemaker. Integration of the present device with a cardiac pacemaker would provide the advantage of e.g., fewer organ-electrode interfaces. It follows, of course, that a sophisticated pacemaker may control the pump and pressure regulator without the need for a second implanted control means (i.e., in the absence of control means 114).

It is understood that the device shown in FIG. 1 presumes the chambers are either attached to the outside of the heart (e.g., by suturing) or placed within a semi-rigid cup such as is that shown and as also is depicted in U.S. Pat. No. 5,169,381, the teaching of which is incorporated by reference herein. Alternatively, a mesh or net arrangement (not shown) may be used in this latter embodiment. The individual chambers 108 would be attached or retained on the inside surface of the cup so as to maintain the relative separation d, d' between the chambers themselves while maintaining the chambers in contact with the heart's surface. The cup or mesh arrangement also causes all expansion of helices 108 to be inwardly directed to create the advantageous bottom-to-top cardiac massage contemplated by this invention.

Referring to FIG. 1 arrows 120 show the general direction of incompressible fluid flow within the system. As is shown, fluid leaves pump 112 passes toward the apex of the heart and then passes through the system toward the heart's base or basal region. It is this direction and the pulse effect given to the fluid via the use of pressure regulator 110 which creates the advantageous cardiac compression wave form which provides the unique cardiac assist of the present invention.

Figure 2:
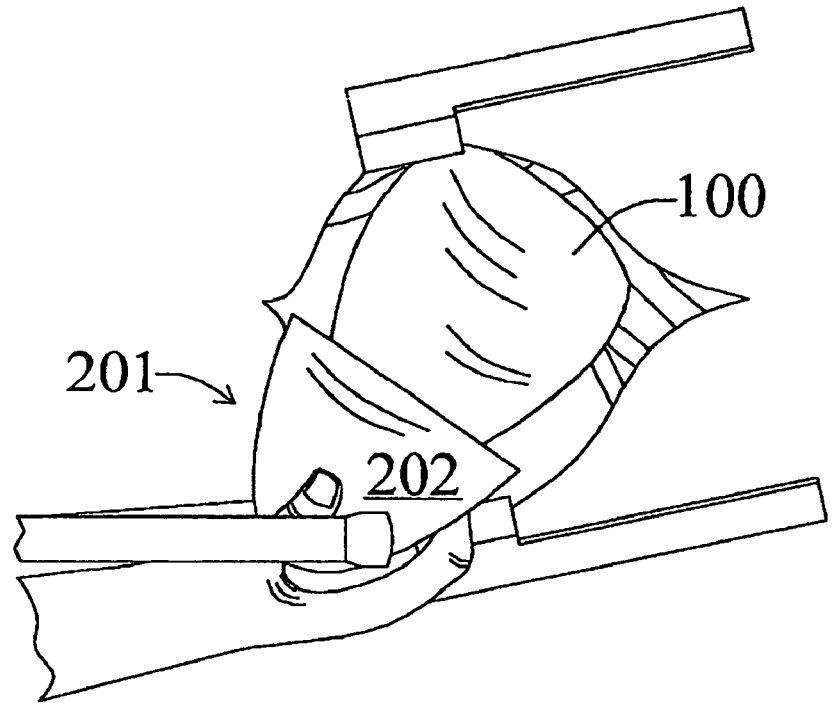
FIG. 2 is a perspective view of a heart massage cup (or apparatus) of the present invention being inserted over a heart.
Figure 3:
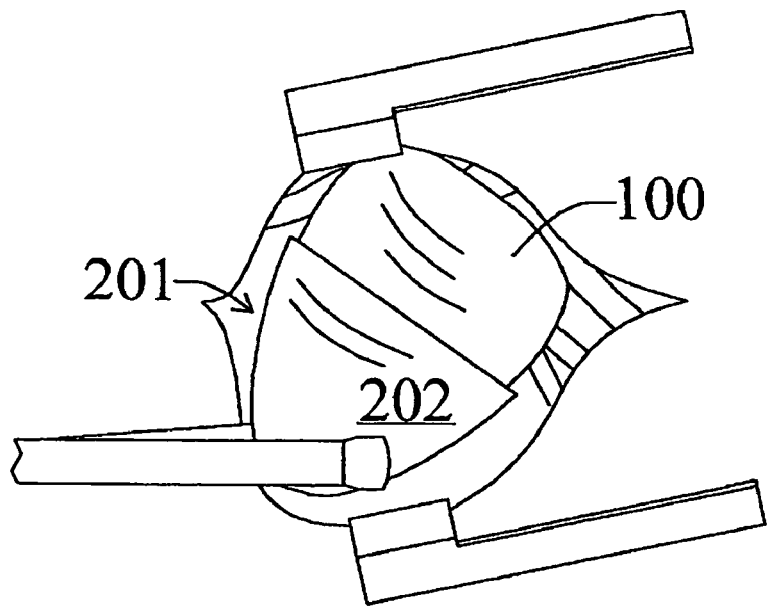
FIG. 3 is a perspective view of the heart massage apparatus of FIG. 2 in place on a heart.

Referencing FIGS. 2 and 3 there is shown an embodiment to the present invention in which a heart-shaped cup member 202 is employed exteriorly of the chamber array 101 discussed above. In this version of cardiac assist device 201 the exterior cup is used to anchor the individual chambers 108 and to maintain their separation distance d, d'. In this version of the invention cup member 202 is merely inserted over the heart 100 and sutured into place. As is shown in FIG. 3 cup member 202 substantially envelopes heart 100 so as to maintain the chamber members 108 in exterior contact with the heart. Partial or complete coverage of heart 100 are both contemplated. Thus, when fluid is pulsed into the helices of the present invention the heart is massaged or compressed in the advantageous fashion described herein thereby generating additional cardiac output.

Figure 4:
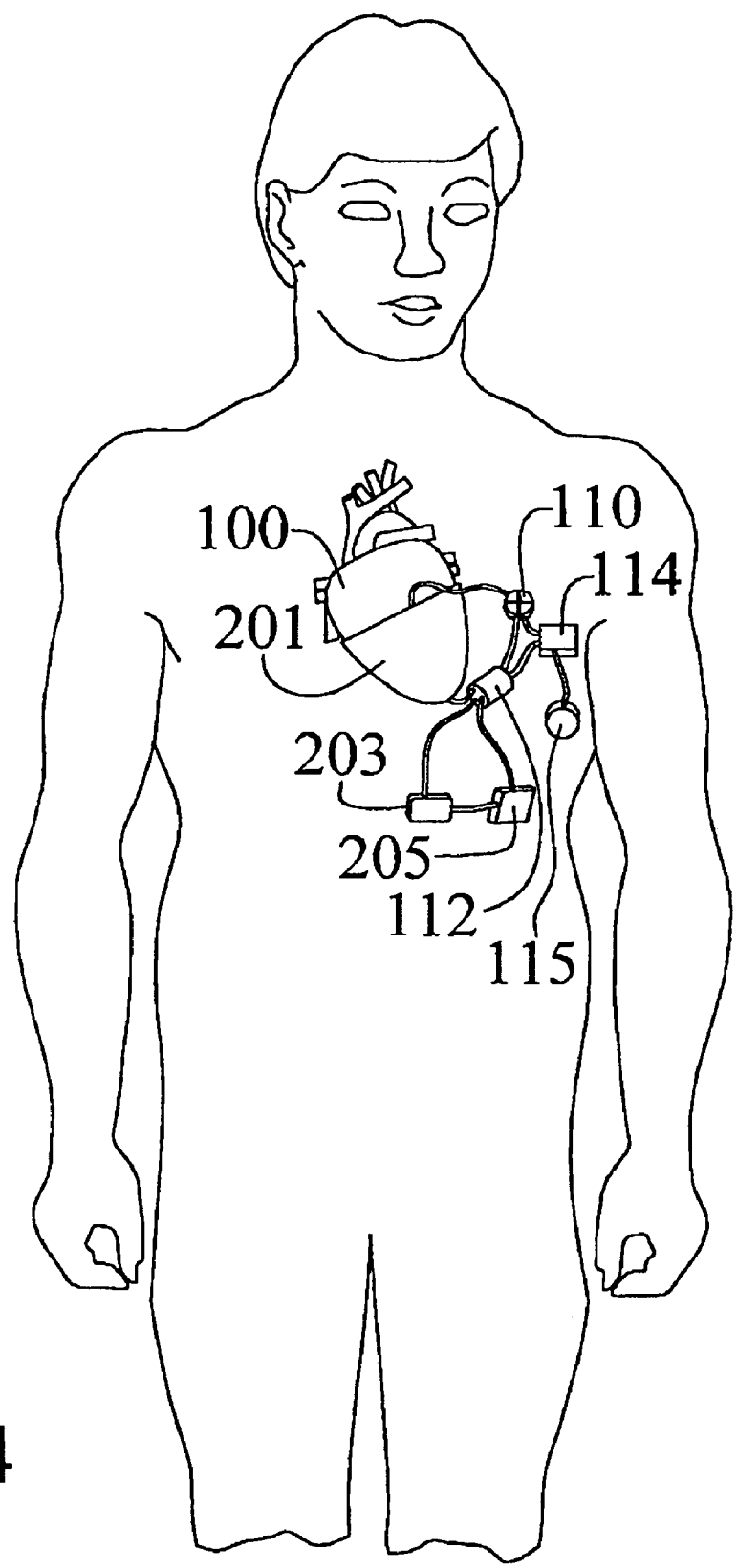
FIG. 4 is a schematic view of the entire system implanted within the human body.

FIG. 4 shows a fully implanted version of the present assist device 201. In addition to the components of the invention shown in FIG. 1 (and which similar designations have been used) there is shown an additional implanted source of electrical energy, e.g., a battery 203 and an implanted fluid reservoir 205. As is shown battery 203 is electrically coupled to pump 112 and, preferably controller 114 while optional fluid reservoir 205 is fluidically coupled to pump 112 to replenish fluid to be pumped through the device 201. Equivalents to optional fluid reservoir 205, e.g., a larger diameter chamber array which would contain sufficient fluid, are within the contemplation of the present invention and will be readily apparent to one skilled in this art.

Figure 5:
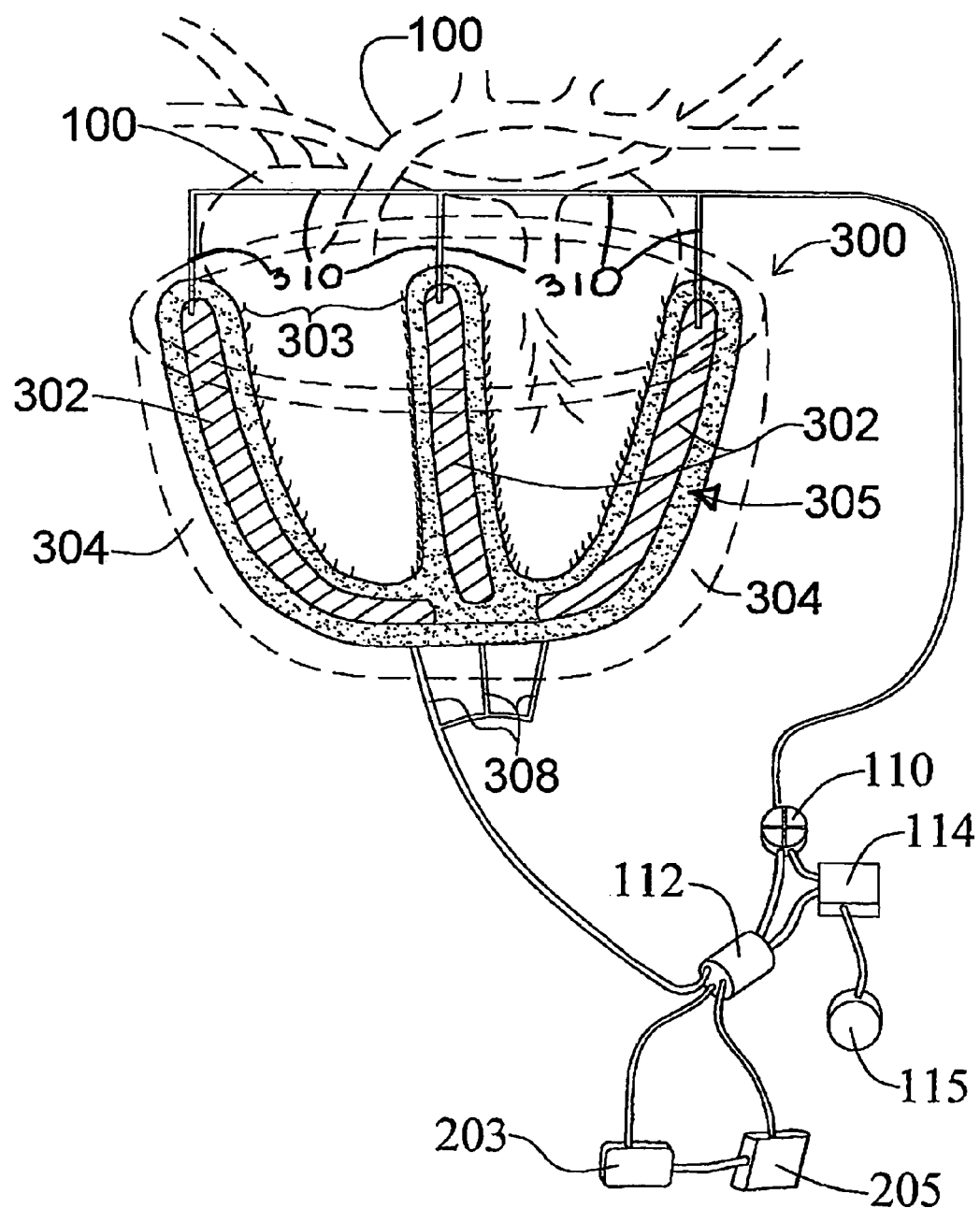
FIG. 5 is a schematic view in partial section, as a second embodiment of the present invention.

FIG. 5 shows schematically, a further embodiment of the present invention in which the chamber array 300 comprises a series of fingers or elongated patches 302 directed around the heart in a palm-open upward fashion. The fingers or patches 302, as shown, are sutured to the exterior of heart 100. Chamber array 300 envelopes heart 100 such that when compressed radially inwardly e.g., by generation of a pulsatile wave or wave form, heart 100 is massaged or compressed in accordance with the invention. Surrounding and enveloping fingers 302 is cup-shaped member 304. Member 304 is substantially radially rigid such that expansion of fingers 302 by pulsatile input of fluid from pump 112 (via input tubes or input connectors 308) causes fingers 302 (or at least the inside surface thereof 303) to be displaced inwardly arrow 305 thereby compress heart 100. Fluid flows from the apex of heart 100 toward its base, pulsatile fluid emerging from fingers 302 into return connector or output connectors 310 to be returned to pressure regulator 110 for reuse. The outside surface 305 of finger 302 is in substantial contact with the inside surface 307 of member 304.

Figure 6:
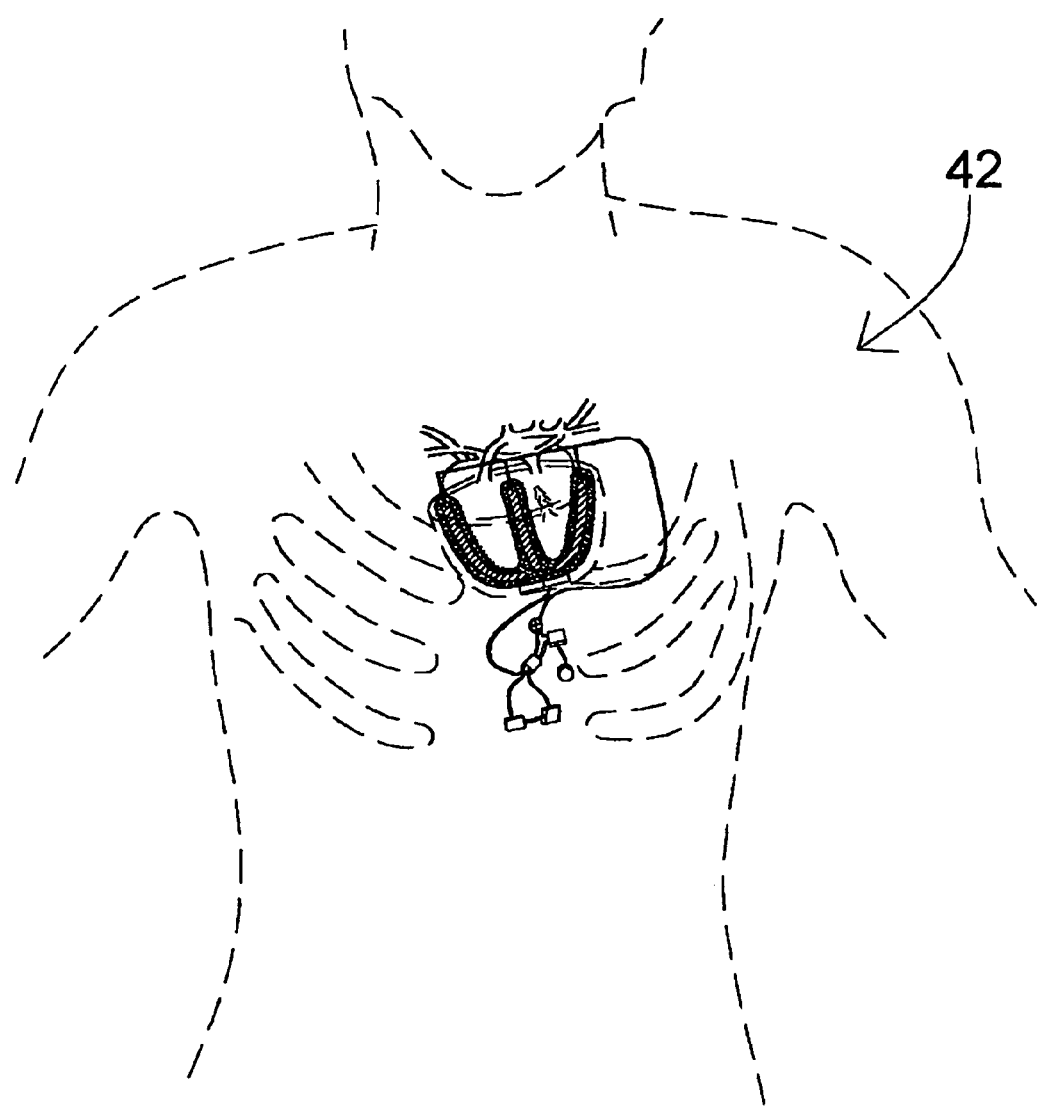
FIG. 6 shows the invention of FIG. 5 fully implanted within the human chest cavity.

FIG. 6 shows the embodiment of the invention of FIG. 5, discussed above, fully implanted within the human chest cavity 42. It should be noted that the devices shown in FIG. 4 and FIG. 6 are not necessarily drawn to the same scale.

Figure 7:
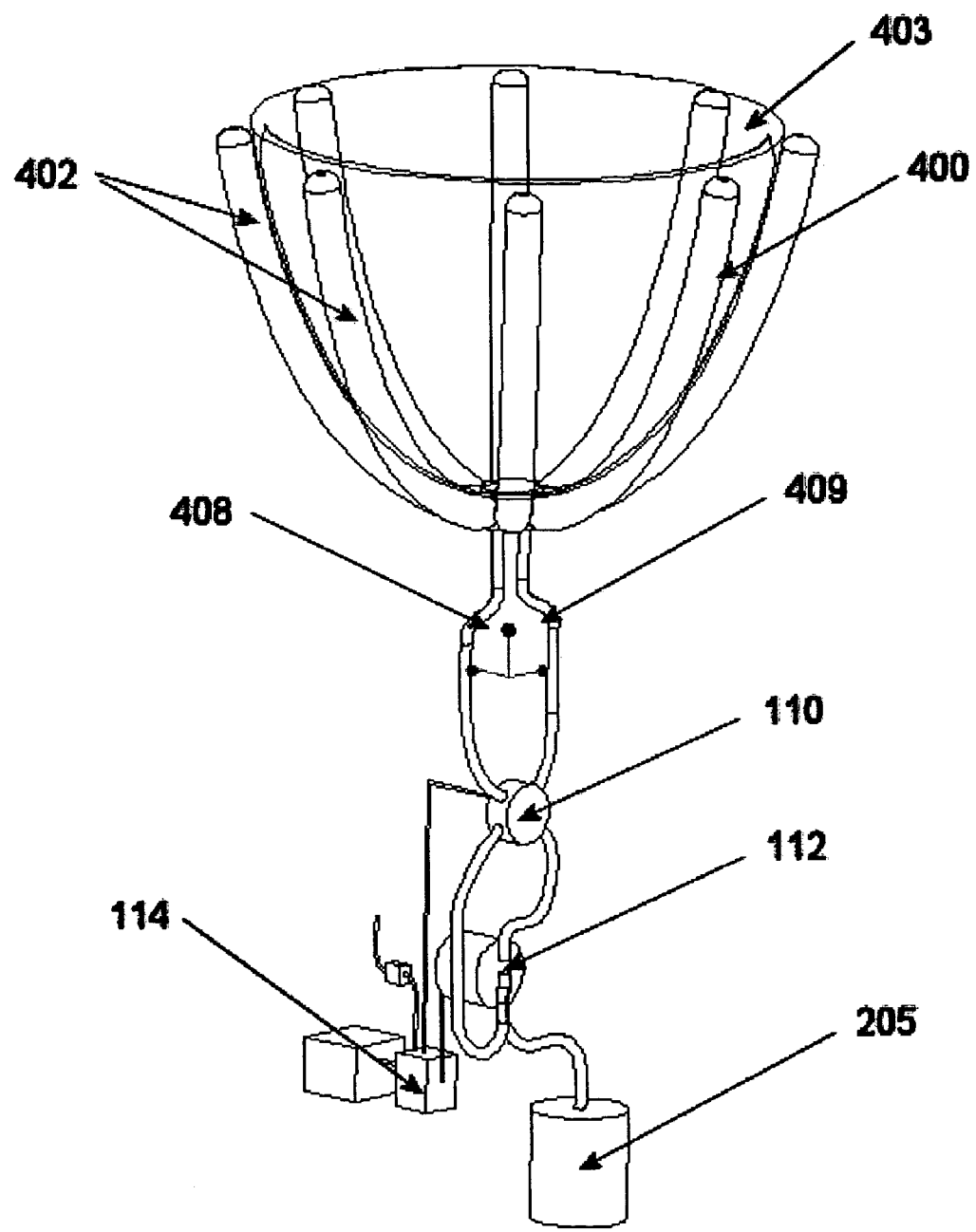
FIG. 7. Is a schematic view of another embodiment of the invention.

FIG. 7 shows schematically, a further embodiment of the present invention in which the chamber array 400 comprises a series of "Bourdon type" fingers or elongated patches 402 directed around the heart in a palm-open upward fashion. Bourdon fingers are made from an elastic material to allow them to expand and contract. The Bourdon type fingers 402, as shown, are sutured to the elastic cup 403 which is sutured to the exterior of heart 100. The Bourdon chamber array envelops heart 100 such that it compresses the heart radially inward by straightening the fingers due to the pulsation of pressure inside the Bourdon tubes, massages the heart in accordance with the invention. The cup-shaped elastic members 403 are substantially radially rigid and hence help the fingers 402 to compress the heart 100 effectively when pulsatile input of fluid from pump 112 (via pressure regulator valve 110 and input tube or input connector 408) cause the elastic fingers 402 to be displaced inwardly thereby massaging heart 100. The pressure generated due to the fluid flow from the pump 112 helps the heart to be massaged from the apex to its base in accordance with the invention. When pressure regulator 110 changes the direction of fluid flow upon the signal received from the microprocessor 114, the backward fluid flow will contract the Bourdon tube fingers outwardly to release the pressure from the heart 100. The outflow of the fluid from the fingers 402 will return through the output connector 409 and pressure regulator valve 110) back into the pump 112 and reservoir 205 for reuse. Bourdon tubes are described in greater detail at pages 444 and 445 of Van Nostrand's *Scientific Encyclopedia*, 8$^{th}$ edition (1995), the entire description of which is incorporated by reference herein.

The present invention has the advantage of providing cardiac assistance or enhancement without creating the kind of blood/device interfaces characteristic of artificial hearts, implanted blood pumps, and other such mechanical, fluid-circulating assist therapies. Thus, blood/interface artifacts, e.g., damage to blood constituents, thrombus creation, and coagulation do not result because the present invention uses only the normal cardiac endothelium to interface with blood.

The present invention is also broadly applicable to cardiac muscle infirmities which are evidenced by weakened cardiac muscle wall and muscle aneurysms or bulges. Such muscular infirmities are evidenced by dyskinetic cardiac muscle segments (i.e., wall segments which do not reliably contract, and hypokinetic segments i.e., wall segments which contract too slowly. Utilization of the present invention with its cardiac cupping or enveloping structure tends to mitigate or eliminate these phenomena. Thus, in one aspect, the present invention is a method of mitigation of cardiac muscle infirmities including dyskinesia and hypokinesia, which method involves the steps of providing a heart-shaped, cup apparatus;

deploying the cup apparatus so that it substantially envelopes a patient's heart evidencing muscle infirmities, the apparatus being located so as to provide exterior support thereto; and anchoring the cup apparatus to the patient's heart.

What is claimed is:

1. An implantable cardiac massage apparatus for providing assistance to a heart having an apex and a base, the apparatus comprising:

a chamber array, the array comprising a series of spaced-apart, fluidically coupled chambers, the array having fluid input and output ports, and the chambers defining an inside surface which closely conforms to the external surface of a heart and;

pressure regulator means, the pressure regulator means being fluidly coupled to the array input port and output port, the pressure regulator means also being fluidically coupled to;

pump means, the pump means and the pressure regulator means being electronically coupled to;

controller means, the controller means being adapted to actuate the pump means and the pressure regulator means so that fluid is pumped, and flows, in only a single direction through the array, the direction being from the input ports to the output ports, the fluid is pumped substantially continuously by the pump means to the input port and the pressure regulator means intermittently inflates and deflates the chambers starting at the apex of the heart to create a rhythmic message of the heart from its apex to its base thereby substantially imitating the natural contraction of the heart, the controller means being further adapted to receive sensor information input from;

a cardiac activity/sensor means, the cardiac activity/sensor means being adapted to sense cardiac activity and input sensor information to the controller means.

2. The apparatus of claim 1 which further includes an implantable reservoir means fluidly coupled to the chamber array.

3. The apparatus of claim 1 which further includes an implantable source of electrical energy electronically coupled to the pump means.

4. The apparatus of claim 1 electronically coupled to the controller means.

5. An apparatus of claim 1 wherein the pressure regulator means comprises a relief valve.

6. An apparatus of claim 1 wherein the pump means comprises a kinetic pump or axial turbine.

7. A method of mechanically assisting a heart comprising the steps of:

deploying an apparatus of claim 1 about the external surface of the heart;

activating the apparatus by energizing the controller means and in turn the pump means so as to cause fluid to flow through the apparatus;

pulsing fluid flow through the apparatus by operating the pressure regulator means the fluid flow starting at the apex of the heart and passing to the base of the heart thereby rhythmically massaging the heart from the apex toward its base to enhance the heart's fluid output in a manner similar to unassisted cardiac discharge.

8. An implantable cardiac massage apparatus for providing assistance to a heart having an apex and a base, the apparatus comprising:

a chamber array, wherein the chamber array comprises elastic Bourdon tubes, the array comprising a series of spaced-apart, fluidically coupled chambers the array having fluid input and output ports, and the chambers defining an inside surface which closely conforms to the external surface of a heart and;

pressure regulator means, the pressure regulator means being fluidly coupled to the array input port and output port, the pressure regulator means also being fluidically coupled to;

pump means, the pump means and the pressure regulator means being electronically coupled to;

controller means, the controller means being adapted to actuate the pump means and the pressure regulator means so that fluid is pumped by the pump means to the input port and the pressure regulator means intermittently inflates and deflates the chambers starting at the apex of the heart to create a rhythmic message of the heart from its apex to its base thereby substantially imitating the natural contraction of the heart, the controller means being further adapted to receive sensor information input from;

a cardiac activity/sensor means, the cardiac activity/sensor means being adapted to sense cardiac activity and input sensor information to the controller means.

9. An implantable cardiac massage apparatus for providing assistance to a heart having an apex and a base, the apparatus comprising:

a helically wound tubing formed into an array, the array defining an inside surface which closely conforms to the external surface of a heart and;

pressure regulator means, the pressure regulator means being fluidly coupled to the array input port and output port, the pressure regulator means also being fluidically coupled to;

pump means, the pump means and the pressure regulator means being electronically coupled to;

controller means, the controller means being adapted to actuate the pump means and the pressure regulator means so that fluid is pumped, and flows, in only a single direction through the array, the direction being from the input ports to the output ports, the fluid is pumped substantially continuously by the pump means to the input port and the pressure regulator means intermittently inflates and deflates the helically wound tubing starting at the apex of the heart to create a rhythmic massage of the heart from its apex to its base thereby substantially imitating the natural contraction of the heart, the controller means being further adapted to receive sensor information input from;

a cardiac activity/sensor means, the cardiac activity/sensor means being adapted to sense cardiac activity and input sensor information to the controller means.

* * * * *